United States Patent
Delisle et al.

(10) Patent No.: US 10,091,301 B2
(45) Date of Patent: Oct. 2, 2018

(54) AUTOMATIC EXTERNAL SENSOR INTERFACE

(71) Applicant: KONINKLIJKE PHILIPS N.V., Eindhoven (NL)

(72) Inventors: Norman Maurice Delisle, Manchester, MA (US); Mashood Puthan Beetil Illikkal, Andover, MA (US); Scott Alan Wuthrich, Reading, MA (US); Simon Edward Kozin, Medford, MA (US)

(73) Assignee: Koninklijke Philips N.V., Eindhoven (NL)

( * ) Notice: Subject to any disclaimer, the term of this patent is extended or adjusted under 35 U.S.C. 154(b) by 204 days.

(21) Appl. No.: 14/901,387

(22) PCT Filed: Jun. 19, 2014

(86) PCT No.: PCT/IB2014/062428
§ 371 (c)(1),
(2) Date: Dec. 28, 2015

(87) PCT Pub. No.: WO2014/207630
PCT Pub. Date: Dec. 31, 2014

(65) Prior Publication Data
US 2016/0154942 A1 Jun. 2, 2016

Related U.S. Application Data

(60) Provisional application No. 61/840,065, filed on Jun. 27, 2013.

(51) Int. Cl.
*H04L 29/08* (2006.01)
*A61N 1/02* (2006.01)
(Continued)

(52) U.S. Cl.
CPC .............. *H04L 67/12* (2013.01); *A61N 1/025* (2013.01); *A61N 1/37252* (2013.01); *G16H 40/63* (2018.01)

(58) Field of Classification Search
CPC ... G06F 19/3406; A61N 1/3925; A61N 1/025; A61N 1/37252; A61N 1/372; G06Q 50/22
See application file for complete search history.

(56) References Cited

U.S. PATENT DOCUMENTS 7,464,360 B2 12/2008 Haji-Aghajani et al.
7,779,183 B2 8/2010 Koehler et al.
(Continued)

FOREIGN PATENT DOCUMENTS

CN 1662083 A 8/2005
CN 102202093 A 9/2011
DE 102005055173 A1 5/2006

*Primary Examiner* — Ajay Ojha

(57) ABSTRACT

A monitor device having a sensor interface includes a connector portion configured to mechanically interface with one or more sensors of a pre-defined type. A hardware interface layer is configured to determine a sensor type and establish a communication interface with the sensor type. A hardware abstraction layer is configured to store a plurality of protocols corresponding with the one or more sensors of a pre-defined type. The hardware abstraction layer communicates with the sensor using a selected protocol for that type through the communication interface to permit interaction between the device and the sensor type.

20 Claims, 5 Drawing Sheets

(51) Int. Cl.
*A61N 1/372* (2006.01)
*G16H 40/63* (2018.01)

(56) References Cited

U.S. PATENT DOCUMENTS

| | | |
|---|---|---|
| 7,937,683 B1 | 5/2011 | Herbst |
| 8,255,026 B1 | 8/2012 | Al-Ali |
| 2002/0184348 A1 | 12/2002 | Rapp et al. |
| 2004/0122490 A1 | 6/2004 | Reinke et al. |
| 2004/0215111 A1 | 10/2004 | Bonutti et al. |
| 2006/0111825 A1 | 5/2006 | Okada et al. |
| 2007/0265674 A1* | 11/2007 | Olson .................. A61N 1/3706 607/37 |
| 2010/0147301 A1 | 6/2010 | Kwok |
| 2011/0144802 A1 | 6/2011 | Jang |
| 2011/0232645 A1 | 9/2011 | Smith |
| 2013/0013107 A1 | 1/2013 | Felique |
| 2013/0066644 A1* | 3/2013 | Dicks .................. A61B 5/0022 705/2 |
| 2013/0109939 A1* | 5/2013 | Spear ....................... A61N 1/08 600/345 |
| 2014/0236029 A1* | 8/2014 | Averina ............... A61N 1/3627 600/508 |
| 2014/0379039 A1* | 12/2014 | Hareland ........... A61N 1/37252 607/2 |

* cited by examiner

AUTOMATIC EXTERNAL SENSOR INTERFACE

This application is a national stage application under 35 U.S.C. § 371 of International Application No. PCT/IB2014/062428 filed on Jun. 19, 2014 and published in the English language on Dec. 31, 2014 as International Publication No. WO 2014/207630 A1, which claims priority to U.S. Application No. 61/840,065 filed on Jun. 27, 2013, the entire disclosures of which are incorporated herein by reference.

BACKGROUND

Technical Field

This disclosure relates to medical instruments and more particularly to an interface connecting system to ensure appropriate hardware is employed in medical applications.

Description of the Related Art

Medical devices that monitor patient vital signs use various types of sensors to convert a patient's physiological activities into electrical signals. The electrical signals can provide a basis for numeric measurements and time-varying waves that can be displayed and used for detecting alarm conditions. An example is a sensor that measures end-tidal carbon dioxide, $EtCO_2$, by measuring the amount of infrared light absorbed in the patient's exhaled breath.

Sensors can be physically mounted internally within a patient monitoring device. Alternatively, they can be manufactured as separate modules with a cable that plugs into a port on the monitoring device. A potential advantage of an external sensor is that the end-user can select which of several alternative, compatible sensor types to employ.

Conventional systems use industry standard interface protocols and universal connectors. An illustrative example of an industry standard interface protocol for medical devices is the Bluetooth Health Device Profile (HDP). This standard defines application programmer interfaces (APIs) for exchanging data with a medical device. Specifically supported devices include sensors such pulse oximeters, blood pressure monitors, blood glucose meters and thermometers. Vendors can design their sensor products to comply with these standard protocols. Any patient monitoring device that implements the associated HDP can exchange data with compliant sensors.

A universal connector is similar to an industry standard protocol in that it defines standard protocol interfaces. In addition, it defines electrical and mechanical or physical interfaces. An example is the Universal Serial Bus (USB). USB allows numerous types of devices to be connected to a host device.

Industry standard protocols and universal connectors are intended for unlimited applicability, allowing new compliant products to be introduced at any time. This universality makes it impossible for the patient monitoring device manufacturer to verify compatibility and safety with each sensor.

SUMMARY

In accordance with the present principles, mechanisms and methods are described for providing a port on a patient monitoring device that will accept a variety of different sensor types and automatically determine which type of sensor is connected. The mechanisms also provide safeguards to ensure that only authorized sensors are employed. In addition, the capabilities of the compatible sensors may be evaluated by the mechanism to ensure that all features or capabilities are understood and can be employed.

In one embodiment, a monitor device having a sensor interface includes a connector portion configured to mechanically interface with one or more sensors of a pre-defined type. Compatibility can be determined using a multi-layer approach. For example, a hardware interface layer, which may be implemented in software, is configured to determine a sensor type and establish a communication interface with the sensor type. A hardware abstraction layer, which may include hardware and software portions, is configured to store a plurality of protocols corresponding with the one or more sensors of a pre-defined type. The hardware abstraction layer communicates with the sensor using a selected protocol for that type through the communication interface to permit interaction between the device and the sensor type.

Another monitor device having a sensor interface includes a connector portion configured to mechanically interface with one or more sensors of a pre-defined type. A three-level mechanism is included for identifying sensor compatibility and providing communication with only compatible sensor types. The three-level mechanism further includes a hardware interface layer configured to determine a sensor type and establish a communication interface with the sensor type; a hardware abstraction layer configured to store a plurality of protocols corresponding with the one or more sensors of a pre-defined type, the hardware abstraction layer communicating with the sensor using a selected protocol for that type through the communication interface to permit interaction between the device and the sensor type; and a device application configured to interact with a compatible sensor through the hardware interface layer and hardware abstraction layer.

A method for verifying compatibility of a sensor type includes determining whether a sensor type is mechanically compatible with a monitoring device by attempting to connect a sensor to the monitoring device; if mechanically compatible, identifying a sensor type using a sensor detection circuit; establishing a communication interface with a mechanically compatible sensor type through a hardware interface layer; and communicating with the sensor type through the communication interface using a selected protocol for that sensor type, the selected protocol being stored in a hardware abstraction layer to permit interaction between the monitoring device and the sensor type.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
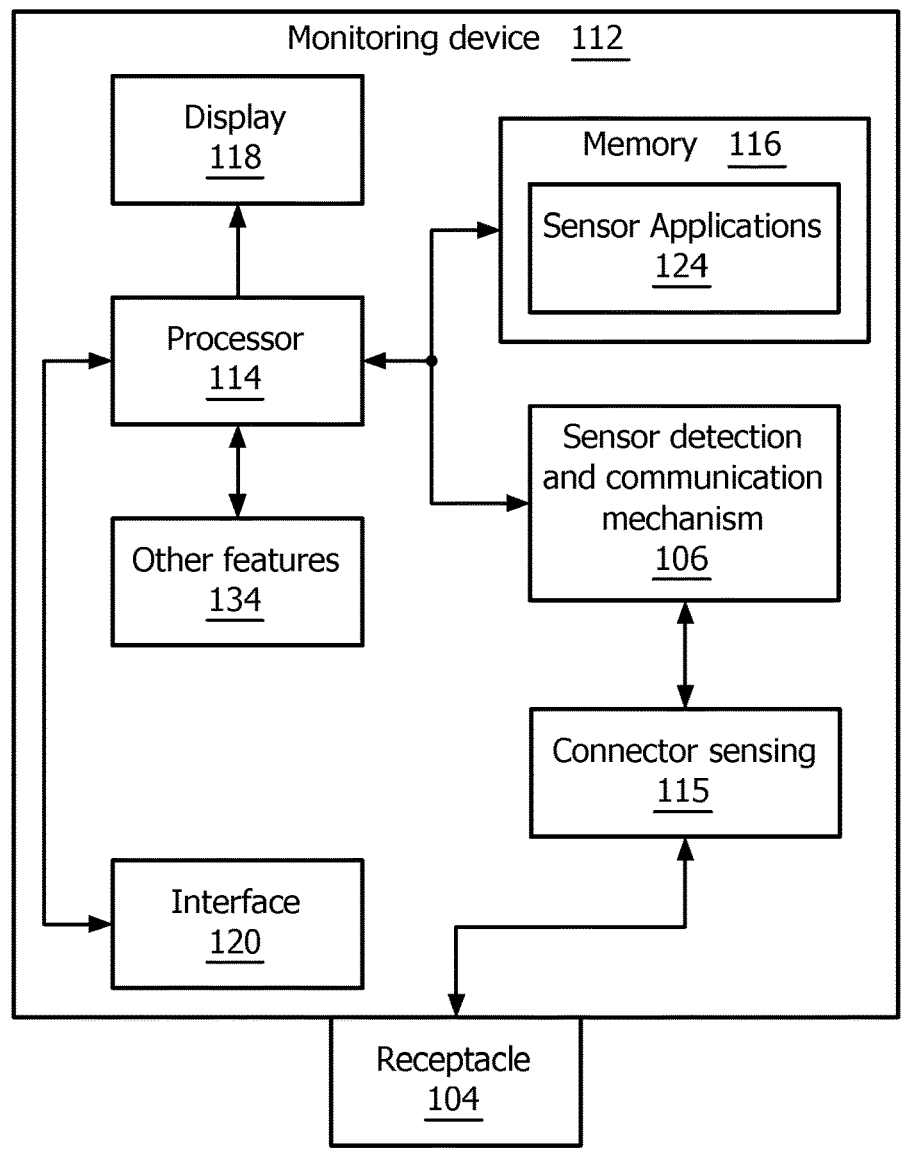
FIG. 1 is a block/flow diagram showing a monitoring device or system having a sensor interface and sensing system in accordance with one embodiment.
Figure 1:
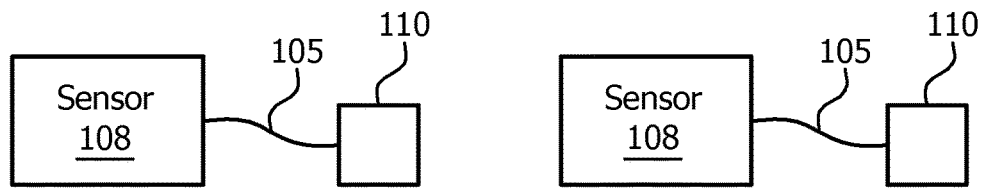

In accordance with the present principles, mechanisms and methods are described for providing a port on a patient monitoring device that will accept a variety of different sensor types and automatically determine which type of sensor is connected. The mechanisms also provide safeguards to ensure that only authorized sensors are employed.

A medical device needs to undergo verification to ensure that the device meets its validated requirements and that the device is safe and effective for clinical usage. When an external sensor is employed with a patient monitoring device, the external sensor is considered to be part of the overall medical device. Therefore, the patient monitoring device needs to be verified and validated for functionality, safety and efficacy with each of its compatible sensors.

In contrast to universal or standardized connectors, the present mechanisms are intended for very limited applicability so that a patient monitoring device manufacturer can pre-select a limited set of compatible sensors and verify that each authorized sensor meets all system-level requirements for functionality, safety and efficacy.

It also should be understood that the present invention will be described in terms of medical instruments; however, the teachings of the present invention are much broader and are applicable to any connectorized instruments or systems. In some embodiments, the present principles are employed in application for complex biological or mechanical systems. In particular, the present principles are applicable to internal tracking or testing devices of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 having a sensor detection and communications module 106. In accordance with one embodiment, the system 100 includes a patient monitoring device 112, such as a defibrillator or other monitor device. The defibrillator or monitor device is illustratively employed as an example. Other devices or systems may also be employed in accordance with the present principles. Device 112 may include one or more processors 114 and memory 116 for storing programs and applications. Sensor detection and communication module 106 may include circuitry for sensor detection. The module 106 may include hardware (logic circuitry), software or combinations of both. In one embodiment, module 106 includes logic gates or circuitry configured to identify and categorize sensors and sensors types. It should be understood that the logic may instead be implemented in software or a combination of hardware and software may be employed. Software portions may be stored memory 116, although other memory elements, e.g., buffers, etc. may be employed.

A connector sensing module 115 is configured to interpret feedback signals from connectors. Connector sensing module 115 may include logic circuitry or may employ any combination of software and circuitry. Connector sensing module 115 communicates with sensors 108 to determine compatibility between the sensors 108 and the monitoring device 112. Compatible sensors 108 may each have a cable 105 with a connector plug 110 that mates with a receptacle port or receptacle 104 on the patient monitoring device 112. Electrical power and signals are routed via pre-defined pins in the connector 104. In addition to power, the electrical connection may include one or more serial data connections, a sensor type identification signal line, and may further include other analog or digital signal lines. The signal lines or cables 105 may include electrical conductors, fiber optics, etc. Within the monitoring device 112, there is a multi-level mechanism for communicating with sensors 108. Upon identification of the sensor or sensors 108, sensor applications 124 stored in memory 116 may be executed to enable proper use of the sensor or sensors 108.

In some embodiments, the monitoring device 112 may include a display 118 to permit a user to interact with the monitoring device 112 and its components and functions, or any other element within the system 100. This is further facilitated by a user interface 120 which may include a keyboard, mouse, a joystick, a haptic device, or any other peripheral or control to permit user feedback from and interaction with the monitoring device 112. The monitoring device 112 may include other features 134 such as electro-shock paddles, other electronic devices or features, etc.

Figure 2:
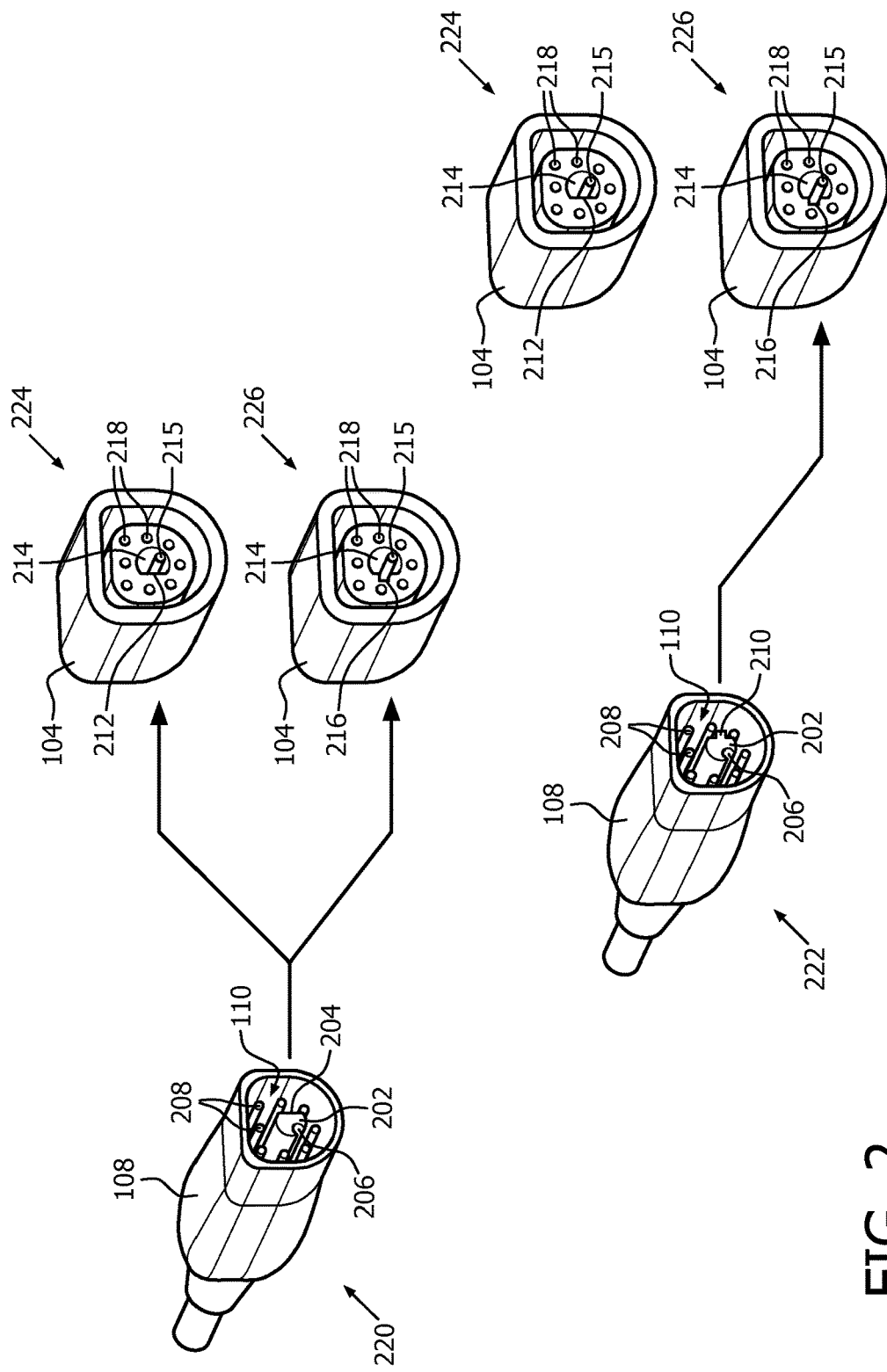
FIG. 2 is a perspective view showing illustrative configurations for plugs and receptacles for deliberately providing mechanically compatible and mechanically incompatible connector pairs in accordance with useful embodiments.

Referring to FIG. 2 with continued reference to FIG. 1, an example depicting hardware connections between the device 112 and sensors 108 is shown to illustratively demonstrate how a receptacle can be made compatible with one sensor or a set of sensors. A receptacle 104 is provided on an exterior surface of the patient monitor device 112. This receptacle 104 physically mates with connector plugs 110 on the external sensors 108. A shape and color of the connector plugs 110 and receptacles 104 may be matched to make it easier for users to locate the correct receptacle or receptacles. In addition, the receptacle 104 is shaped and/or keyed to fit all compatible sensors 108, and only compatible sensors.

A connector keying strategy can be implemented with multiple levels to permit varying combinations of sensors 108 and monitoring devices (112). For example, receptacle 226 supports sensors 220 and 222. But, receptacle 224 only supports sensor 220. Sensors 220 and 222 include a plurality of conductors or pins 208. A center plug portion 202 includes a groove 206 and flat 204 or a key 210, respectively for sensor 220 and sensor 222. The key 210 is designed so that receptacle 224 will not mate with sensor 222. The receptacles 224 and 226 include a key way 214 and a conductive rib 215 that is received in groove 206. Receptacle 224 includes a mating flat 212, and receptacle 226 includes a mating slot 216. The flat 204 fits the mating flat 212. The pins 208 are received in sockets 218. The sensor 220 with the flat 204 fits both receptacles 224 and 226. The sensor 222 with the key 210 fits the receptacle 226 only. It should be understood that this example represents but one illustrative scheme and other arrangements are contemplated. Additional features, e.g., keys or slots, may be provided on sensors 220 or 222 or receptacles 224 and 226 to provide more permutations/combinations, as needed.

The electrical signal levels and connections (e.g., pins 208 to sockets 218) provided in the interface need to match the requirements of all compatible sensors. The connector pins 208 used for power, ground and data signals need to be compatible for all working sensor/receptacle pairs.

Figure 3:
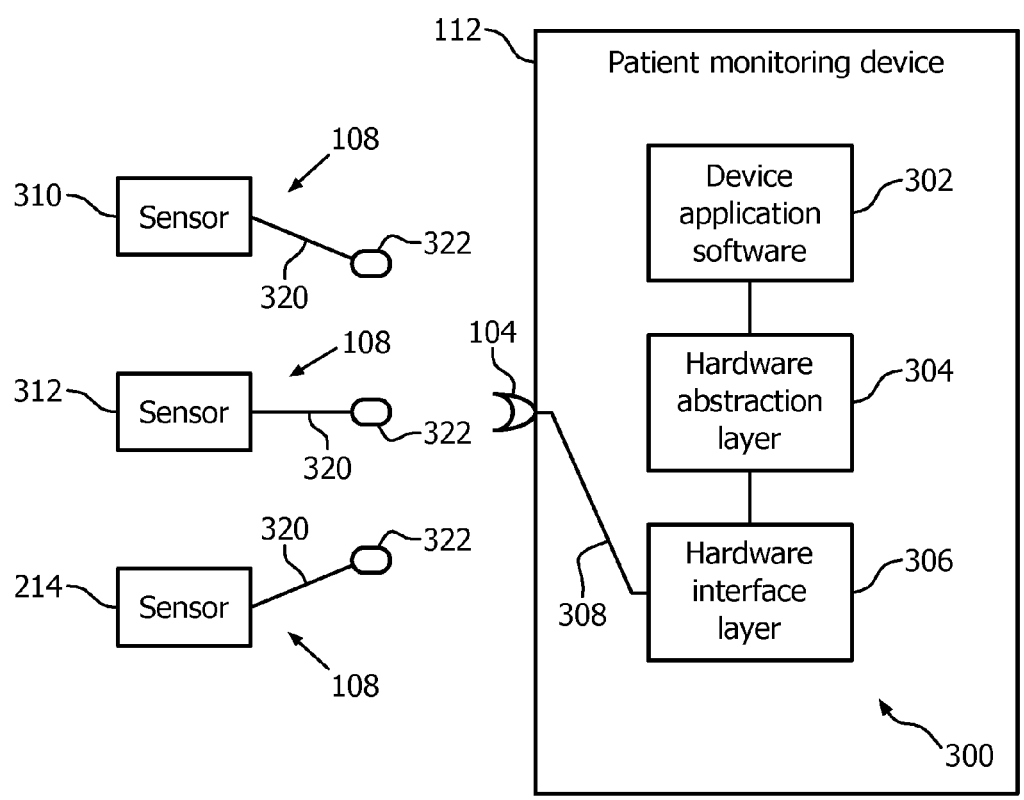
FIG. 3 is a block/flow diagram showing a three-level mechanism for identifying and communicating with sensors in accordance with one embodiment.

Referring to FIG. 3 with continued reference to FIG. 1, within the monitoring device 112, there is a three-level mechanism 300 for sensor detection and communication with sensors 108. In FIG. 1, the three layer mechanism 300 is included in the connector sensing module 115, the sensor detection and communications module 106 and the sensor applications 124. In FIG. 3, the three layer mechanism 300 translates to a hardware interface layer 306, a hardware abstraction layer 304 and a device application software layer 302, respectively.

If the sensor 108 mechanically fits into the receptacle of the monitoring device 112, the monitoring device 112 needs to determine if the sensor 108 is compatible on a connection/signal level through a combination of a hardware sensor detection circuit or hardware interface layer 306 and a software confirmation of a compatible protocol using one or more of a hardware abstraction layer 304 and/or device application software 302. The device 112 can then employ verified software and protocols to communicate with an identified compatible sensor.

In one illustrative embodiment, a monitor/defibrillator is employed for device 112. The device 112 is compatible with several types of external $EtCO_2$ sensors, e.g., types 310, 312, 314. The $EtCO_2$ sensors are supplied by different manufacturers and include both sidestream and mainstream $CO_2$ measurement technologies, for example, Philips® provides an external mainstream sensor (Capnostat 5™) and an external sidestream sensor (LoGlo™) and Covidien™ (Oridion™) provides an external sidestream sensor (MicroPod™). The sensors 108 in this example include three types 310, 312, and 314.

The alternative compatible sensors 108 each have a cable 320 with a connector plug 322 that mates with the receptacle port 104 on the patient monitoring device 112. Electrical power and signals are routed via pre-defined pins in the connectors (plugs 322 to receptacle 104). In addition to power, the electrical connection may include one or more serial data connections, a sensor-type identification signal line, a fiber optic link, a wireless link (e.g., between the plugs 322 and respective sensor types 310, 312, 314) and any other analog or digital signal lines. It should be understood that while the receptacle 104 appears on the device 112; the device 112 may include a plug for engaging a receptacle of the sensor or combinations of plus and receptacles may be employed.

Figure 4:
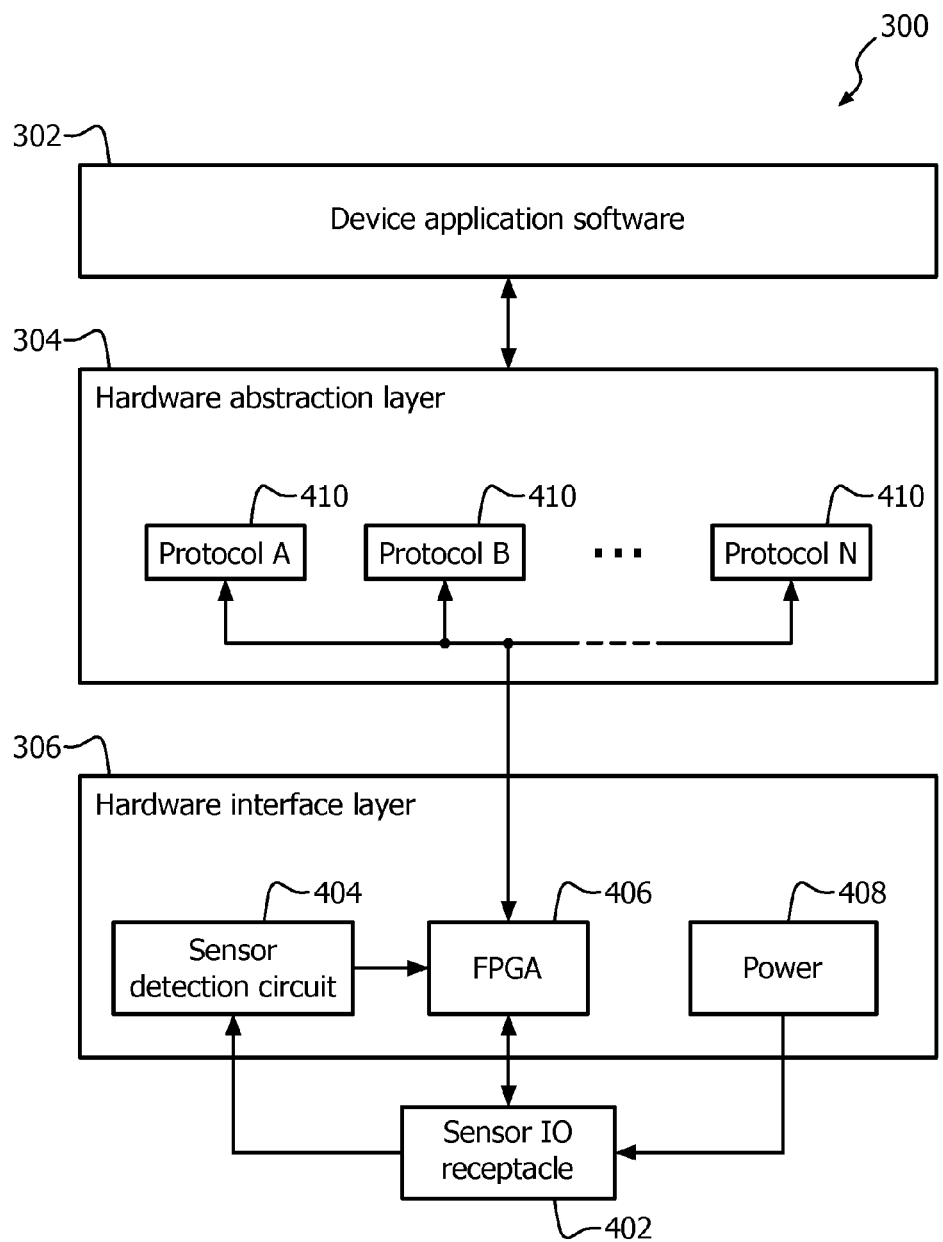
FIG. 4 is a block/flow diagram showing the three-level mechanism of FIG. 3 in greater detail in accordance with one embodiment.

Referring to FIG. 4, the three-level mechanism 300 for sensor detection and communication is shown in greater detail. The hardware interface layer 306 includes a sensor detection circuit 404, a multiplexing device, such as a field programmable gate array (FPGA) 406, and a power regulation circuit 408. The sensor detection circuit 404 determines whether a sensor is connected, e.g., an open is detected on the sensor type identification signal line when there is no sensor connected to a sensor input/output (IO) receptacle 402 (see also receptacle 104). When a sensor is connected, the sensor outputs a signal on the sensor type signal line that uniquely indicates the type of sensor (e.g., sensor type 310, 312, 314, etc.) that is connected.

The sensor detection circuit 404 may include a logic circuit. The output of the sensor detection circuit 404 may include the following possible logical values: No sensor connected; Unrecognized sensor connected; Sensor type 310 connected, Sensor type 312 connected; and so on, for other compatible sensors. The FPGA 406 provides interfaces for the software of the hardware abstraction layer 304 to access the output of the sensor detection circuit 404, plus the FPGA 406 includes a universal asynchronous receiver/transmitted (UART) for serial data communications with the sensor through receptacle 402. The hardware interface layer 306 also provides regulated power for the sensor connected to the receptacle 402 using the power regulation circuit 408.

The hardware abstraction layer 304 provides flexibility in the type of protocol and therefore the type of sensors employed with the device 112. The hardware abstraction layer 304 does not require that the same data communications protocol be used by all compatible sensors. Each of the sensor types could use a different communications protocol over the serial data connection. A middle layer (304) of the mechanism includes a plurality of stored protocols 410 (e.g., protocols A to N). The hardware abstraction layer 304 automatically adapts to use the protocol 410 with the connected sensor. The software executing within the hardware abstraction layer 304 checks the output of the sensor detection circuit 404 (via the FPGA 406) periodically to determine whether a sensor has been plugged in. When a sensor is connected, the output of the sensor detection circuit 404 is used to determine which sensor protocol 410 to employ.

The device's selected sensor protocol software (protocol 410) sets the baud rate and attempts to communicate with the connected sensor (402) using its protocol. If the sensor does not correctly respond to that protocol, the sensor is not compatible, and an error message is presented on the monitoring device display 118 (FIG. 1). If the sensor correctly responds, the device 112 has determined which type of sensor is connected and the verified software protocols 410 for that sensor are used to communicate with the sensor. The device 112 also presents an error message if the sensor detection circuit indicates that an incompatible sensor has been connected.

Since the hardware abstraction layer 304 provides transparency with respect to the type of sensor connected, the device application software 302 does not need custom communications software for each sensor. The complexity of dealing with multiple sensors is encapsulated in the hardware abstraction layer 304. The device application software 302 is responsible for supporting any functions that are specific to a type of sensor. For example, one type of sensor may need to be calibrated or various types of sensors might detect different error conditions. The device application software 302 handles the calibration method, generation of error messages, etc.

The device application software 302 may also control data acquisition functions, check specifications for the sensors, etc. In accordance with the present principles, a user can connect any of several different types of sensors, and the monitoring device 112 will automatically recognize which sensor is connected. The sensor type that is connected will not only be recognized but will provide the monitoring device 112 with an understanding of the sensor's capabilities based on the sensor type. In this way, the sensor plugged into the receptacle will have its full functionality available for use.

Figure 5:
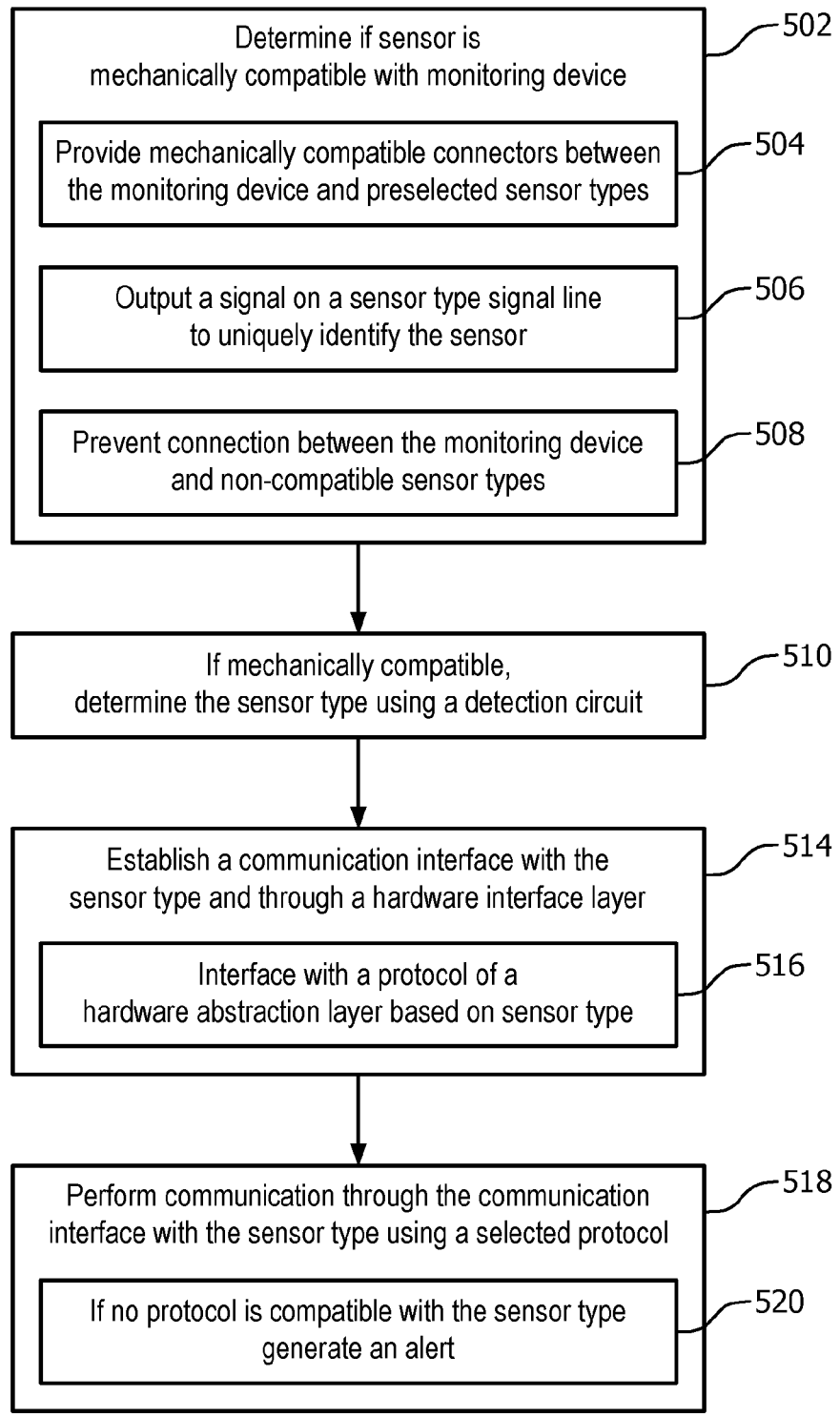
FIG. 5 is a flow diagram showing a method for identifying and communicating with sensors in accordance with illustrative embodiments.

Referring to FIG. 5, a method for verifying compatibility of a sensor type is illustratively shown in accordance with useful embodiment. In block 502, a determination of whether a sensor type is mechanically compatible with a monitoring device is made by attempting to connect a sensor to the monitoring device. In block 504, this may include providing mating connectors to have mechanical compatibility between the monitoring device and preselected sensor types. The preselected sensor types are determined in advance to be compatible with the monitoring device. In block 506, a signal that is output on a sensor type signal line is provided to uniquely indicate the sensor type. In block 508, connection to the monitoring device is prevented for sensors not of the pre-defined type by providing connector portions with non-compatible engagement features.

In block 510, if mechanically compatible, a sensor type is identified using a sensor detection circuit. A sensor, which is not mechanically compatible, could not be connected to the monitoring device as described in block 508. In block 514, a communication interface is established with a mechanically compatible sensor type through a hardware interface layer. This may include a multiplexing device or FPGA to make interface connections across a hardware interface layer. In block 516, establishing the communication interface includes interfacing with a protocol of a hardware abstraction layer in accordance with an output of the sensor detection circuit.

In block 518, communication with the sensor type is performed through the communication interface using a selected protocol for that sensor type. The selected protocol is stored in a hardware abstraction layer to permit interaction between the monitoring device and the sensor type. In block 520, if no protocol is compatible with the sensor type, a user is alerted that the sensor is not compatible with the monitoring device.

In interpreting the appended claims, it should be understood that:
  a) the word "comprising" does not exclude the presence of other elements or acts than those listed in a given claim;
  b) the word "a" or "an" preceding an element does not exclude the presence of a plurality of such elements;
  c) any reference signs in the claims do not limit their scope;
  d) several "means" may be represented by the same item or hardware or software implemented structure or function; and
  e) no specific sequence of acts is intended to be required unless specifically indicated.

Having described preferred embodiments for an automatic external sensor interface (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A monitor device having a sensor interface, comprising:
  a connector portion configured to mechanically interface with one or more sensors of a pre-defined type;
  a hardware interface layer configured to determine a sensor type and establish a communication interface with the sensor type; and
  a hardware abstraction layer configured to store a plurality of protocols corresponding with the one or more sensors of a pre-defined type, the hardware abstraction layer communicating with the sensor using a selected protocol for that type through the communication interface to permit interaction between the device and the sensor type.

2. The device as recited in claim 1, wherein the hardware interface layer includes a sensor detection circuit configured to sense when a sensor is connected and to determine the sensor type.

3. The device as recited in claim 2, wherein the hardware interface layer includes a multiplexing device configured to interface protocols of the hardware abstraction layer in accordance with an output of the sensor detection circuit.

4. The device as recited in claim 3, wherein the multiplexing device includes a field programmable gate array having a universal asynchronous receiver/transmitted (UART) for serial data communications with a sensor connected to the device.

5. The device as recited in claim 1, wherein the hardware interface layer includes a power regulation circuit to provide regulated power for a sensor connected to the device.

6. The device as recited in claim 1, wherein the connector portion includes engagement features that prevent connection by sensors not of the pre-defined type.

7. The device as recited in claim 1, wherein the device includes a defibrillator.

8. A monitor device having a sensor interface, comprising:
a connector portion configured to mechanically interface with one or more sensors of a pre-defined type; and
a three-level mechanism for identifying sensor compatibility and providing communication with only compatible sensor types, the three-level mechanism further comprising:
   a hardware interface layer configured to determine a sensor type and establish a communication interface with the sensor type;
   a hardware abstraction layer configured to store a plurality of protocols corresponding with the one or more sensors of a pre-defined type, the hardware abstraction layer communicating with the sensor using a selected protocol for that type through the communication interface to permit interaction between the device and the sensor type; and
   a device application configured to interact with a compatible sensor through the hardware interface layer and hardware abstraction layer.

9. The device as recited in claim 8, wherein the hardware interface layer includes a sensor detection circuit configured to sense when a sensor is connected and to determine the sensor type.

10. The device as recited in claim 9, wherein the hardware interface layer includes a multiplexing device configured to interface protocols of the hardware abstraction layer in accordance with an output of the sensor detection circuit.

11. The device as recited in claim 10, wherein the multiplexing device includes a field programmable gate array having a universal asynchronous receiver/transmitted (UART) for serial data communications with a sensor connected to the device.

12. The device as recited in claim 8, wherein the hardware interface layer includes a power regulation circuit to provide regulated power for a sensor connected to the device.

13. The device as recited in claim 8, wherein the connector portion includes engagement features that prevent connection by sensors not of the pre-defined type.

14. The device as recited in claim 8, wherein the device includes a defibrillator.

15. A method for verifying compatibility of a sensor type, comprising:
   determining whether a sensor type is mechanically compatible with a monitoring device by attempting to connect a sensor to the monitoring device;
   if mechanically compatible, identifying a sensor type using a sensor detection circuit;
   establishing a communication interface with a mechanically compatible sensor type through a hardware interface layer; and
   communicating with the sensor type through the communication interface using a selected protocol for that sensor type, the selected protocol being stored in a hardware abstraction layer to permit interaction between the monitoring device and the sensor type.

16. The method as recited in claim 15, wherein determining whether a sensor type is mechanically compatible includes providing mating connectors to have mechanical compatibility between the monitoring device and preselected sensor types.

17. The method as recited in claim 15, wherein determining whether a sensor type is compatible with a monitoring device includes outputting a signal on a sensor type signal line to uniquely indicate the sensor type.

18. The method as recited in claim 15, wherein establishing a communication interface includes interfacing a protocol of the hardware abstraction layer in accordance with an output of the sensor detection circuit.

19. The method as recited in claim 15, further comprising if no protocol is compatible with the sensor type, alerting a user that the sensor is not compatible with the monitoring device.

20. The method as recited in claim 15, further comprising preventing connection to the monitoring device by sensors not of the pre-defined type by providing connector portions with non-compatible engagement features.

* * * * *